United States Patent
Yang et al.

(10) Patent No.: US 11,608,502 B2
(45) Date of Patent: Mar. 21, 2023

(54) RNAI NANO-PREPARATION, PREPARATION METHOD THEREOF AND APPLICATION THEREOF IN TMV PREVENTION AND CONTROL

(71) Applicants: TOBACCO RESEARCH INSTITUTE OF CHINESE ACADEMY OF AGRICULTURAL SCIENCES, Qingdao (CN); SICHUAN BRANCH OF CHINA TOBACCO, Chengdu (CN); LIANGSHAN BRANCH OF SICHUAN TOBACCO, Xichang (CN)

(72) Inventors: Jinguang Yang, Qingdao (CN); Fenglong Wang, Qingdao (CN); Xiang Xu, Qingdao (CN); Ying Li, Qingdao (CN); Liyun Song, Qingdao (CN); Lili Shen, Qingdao (CN); Qiang Lei, Chengdu (CN); Changchun Feng, Chengdu (CN); Bin Li, Chengdu (CN); Yong Wang, Xichang (CN); Dongyang Liu, Xichang (CN); Lianqiang Jiang, Xichang (CN)

(73) Assignees: TOBACCO RESEARCH INSTITUTE OF CHINESE ACADEMY OF AGRICULTURAL SCIENCES, Qingdao (CN); SICHUAN BRANCH OF CHINA TOBACCO, Chengdu (CN); LIANGSHAN BRANCH OF SICHUAN TOBACCO, Xichang (CN)

(*) Notice: Subject to any disclaimer, the term of this patent is extended or adjusted under 35 U.S.C. 154(b) by 0 days.

(21) Appl. No.: 16/998,957

(22) Filed: Aug. 20, 2020

(65) Prior Publication Data
US 2021/0363529 A1 Nov. 25, 2021

(30) Foreign Application Priority Data
May 25, 2020 (CN) .......................... 202010453286.4

(51) Int. Cl.
| C12N 15/11 | (2006.01) |
| C12N 15/113 | (2010.01) |
| A01N 25/04 | (2006.01) |
| A01N 57/16 | (2006.01) |
| A01N 63/60 | (2020.01) |

(52) U.S. Cl.
CPC .......... *C12N 15/1131* (2013.01); *A01N 25/04* (2013.01); *A01N 57/16* (2013.01); *A01N 63/60* (2020.01); *C12N 15/113* (2013.01); *C12N 2310/14* (2013.01); *C12N 2310/141* (2013.01); *C12N 2320/32* (2013.01)

(58) Field of Classification Search
CPC .................................................. C12N 15/1131
See application file for complete search history.

(56) References Cited

U.S. PATENT DOCUMENTS

2018/0072633 A1* 3/2018 Dent ........................ C05F 11/08

* cited by examiner

*Primary Examiner* — Ekaterina Poliakova-Georgantas
(74) *Attorney, Agent, or Firm* — Nitin Kaushik

(57) ABSTRACT

The invention belongs to the field of genetic engineering technology and application thereof, and in order to solve the problems of lack of high efficient TMV-resistant RNAi nano-preparation at present, complicated preparation process of medicament, poor stability and delivery efficiency of dsRNA, the invention provides an RNAi nano-preparation, preparation method thereof and application thereof in TMV prevention and control. The RNAi nano-preparation is prepared from dsRNA and chitosan nano materials, wherein, dsRNA is a highly TMV-resistant RdRP3 gene with a length of 313 bp obtained from screening, with nucleotide sequence shown in SEQ ID NO.1, and the volume ratio of the chitosan to 1 μg/μl dsRNA is 10:(1-6). The RNAi nano-preparation provided by the invention has the advantages of stronger stability and better durability of dsRNA, good biocompatibility, good biodegradability, no harm to crops, environmental friendliness and the like, and has a good application prospect in the field of TMV virus prevention and control.

3 Claims, 9 Drawing Sheets

Specification includes a Sequence Listing.

RNAI NANO-PREPARATION, PREPARATION METHOD THEREOF AND APPLICATION THEREOF IN TMV PREVENTION AND CONTROL

INCORPORATION BY REFERENCE

The sequence listing provided in the file entitled Sequence_Listing_Edited_FINAL.txt, which is an ASCII text file that was created on Aug. 20, 2020, and which comprises 5243 bytes, is hereby incorporated by reference in its entirety.

TECHNICAL FIELD

The invention belongs to a gene engineering technology and an application field thereof, and particularly relates to an RNAi nano-preparation, a preparation method thereof and an application thereof in TMV prevention and control, in particular to an efficient targeted gene screening, a simple preparation method of the RNAi nano-preparation and a new application thereof in TMV prevention and control.

BACKGROUND ART

Chitosan is obtained by deacetylation of chitin, which widely exists in nature. Because of its good safety, biocompatibility and microbial degradation, chitosan has been widely studied and applied in the fields of plant protection, biological therapy, genetic engineering, food and medicine. Tobacco mosaic virus (TMV) is widely distributed in various tobacco regions in China TMV is the most widely distributed and common virus disease in tobacco at present, and has great harm to tobacco. After being infected by virus, the growth and development of plants will be seriously affected, and the yield will be reduced seriously, which poses a threat to the economy of tobacco-growing areas.

In recent years, delivery of dsRNA or siRNA through nanomaterials has become a hot research trend, which can solve the problems of poor self-stability and easy degradation of dsRNA or siRNA and achieve the purpose of effectively preventing and controlling some plant viral diseases. This technology has many advantages, such as environment-friendly, long-lasting and harmless to crops, and can effectively prevent and control plant viruses.

Although RNAi nano-preparation have been studied in prevention and control of TMV virus, few studies have been done on the screening of highly effective fragments, so after the highly effective fragments are screened, the ideas of the prior art are effectively utilized to prepare highly effective nano-preparation, and the preparation is applied to TMV virus prevention and control, which has very important significance for large-scale virus prevention and control.

SUMMARY OF THE INVENTION

In order to solve the problems of lack of high efficient TMV-resistant RNAi nano-preparation at present, complicated preparation process of medicament, poor stability and delivery efficiency of dsRNA, the invention provides an RNAi nano-preparation, preparation method thereof and application thereof in TMV prevention and control, which screens high-efficiency fragments resisting TMV replication, proliferation and movement, provides a simple preparation method of the RNAi nano-preparation and applies it to the process of TMV prevention and control.

In order to achieve the above object, the invention adopts the following specific technical scheme: an RNAi nano-preparation, characterized in that the RNAi nano-preparation is prepared from dsRNA and chitosan nano materials, wherein, the dsRNA is a highly TMV-resistant RdRP3 gene with a length of 313 bp obtained from screening, with nucleotide sequence shown in SEQ ID NO.1, and the volume ratio of the chitosan to 1 µg/µl dsRNA is 10:1-6.

Further,

Further, a target gene of the dsRNA is an RNA-dependent RNA polymerase protein gene (RdRP3 gene) in TMV genes.

Further, dropwise adding a dsRNA solution into a chitosan nano material solution in proportion, uniformly mixing, slowly adding the dsRNA-containing chitosan solution into a 1% SDS solution at a ratio of 2:1, shaking for 10 min, and wrapping the dsRNA inside the chitosan to form spheroids with a diameter of 100-200 nm; wherein, the concentration of the dsRNA solution is 1 µg/µl; the chitosan nano material solution is prepared by dissolving chitosan in glacial acetic acid, and the final concentration of the chitosan nano material solution is 2 µg/µl.

Further, the preparation method of the dsRNA solution comprises the following specific steps of:

(1) extracting total RNA of tobacco leaves infected by TMV, and carrying out reverse transcription with the extracted total RNA as a template to obtain cDNA;

(2) selecting a gene of a protein related to TMV replication, proliferation and movement in plants, carrying out real-time RT-PCR and Western Blot verification by taking the expression level of TMV CP protein as an index, and screening to obtain a highly resistant RdRP3 gene with the length of 313 bp;

(3) designing specific amplification primers of RdRP3 by taking cDNA as a template, and amplifying a target gene fragment by using the specific primers;

(4) synthesizing dsRNA in vitro by using target gene fragments obtained from specific amplification as a template.

Further, the method for extracting total RNA of TMV infected tobacco leaves is a Trizol extraction method.

Further, the upstream primer sequence and the downstream primer sequence of the specific amplification primer of the RdRP3 sequence are the DNA sequences shown in SEQ ID NOs.2 and 3.

Further, the use method of the RNAi nano-preparation is uniformly spreading or spraying a finished solution on plant leaves.

The RNAi nano-preparation prepared by the invention has the characteristics of strong stability, high delivery efficiency and difficulty in degradation, and can increase the drug effect by promoting the shuttling and transfer efficiency of dsRNA in plants, thereby effectively preventing and controlling TMV.

The invention focus on creating a non-transgenic RNAi interference system special for tobacco, through coordination polymerization technology, new nano-drugs were developed by coating antiviral dsRNAs with nanomaterials, which were stably present on the surface of tobacco plants and continuously released into the body to exert antiviral activity, and reconstruct tobacco specific antiviral immune system.

The invention has important theoretical significance and great practical value for development and application of novel plant virus agents, shows great potential of preventing and controlling TMV in the field, and promotes practice and development of tobacco disease management based on RNAi.

Through comparison in many aspects, the invention screens a gene sequence with the best anti-TMV effect, uses excellent nano-material chitosan, and simplifies the preparation method of the composite nano-preparation, so that the method is simpler and more convenient, and the prevention and control effect is more efficient and obvious.

In order to develop novel plant antiviral nano-drugs, six candidate genes were preliminarily selected, the corresponding dsRNA was synthesized in vitro, and the antiviral ability was evaluated by biological methods with the activity of anti-tobacco mosaic virus as the index. On this basis, the dsRNA which can efficiently degrade TMV target nucleic acid is screened, and the screened antiviral high-efficiency fragments are coated with chitosan to achieve more efficient delivery and targeted silencing.

Compared with the prior art, the advantages and positive effects of the invention are as follows:

(1) combined with the results of real-time RT-PCR and Western Blot analysis, the invention selects a gene fragment RdRP3, with stable and significant differential expression, which can efficiently bind to the target gene, reduce the expression amount of tobacco mosaic virus in infected plants, and realize targeted RNAi protection of plants.

(2) the invention provides an application of RNAi nano-preparation in the prevention and control of TMV. The corresponding dsRNA, is synthesized in vitro by RNA-dependent RNA polymerase RdRP group of TMV as a template, and the stability of dsRNA is improved by combining with chitosan nano-material, so that it can enter the plant more stably and cause RNAi in the plant body.

(3) the preparation provided by the invention, using chitosan as a carrier, can not only increase the stability of dsRNA, but also improve the transfection efficiency of dsRNA nanoparticles.

(4) the RNAi nano-preparation provided by the invention can be applied to TMV prevention and control by spraying or fertilizing.

(5) the RNAi nano-preparation provided by the invention can be used as a nano-biopesticide and applied to related production in agriculture.

DETAILED DESCRIPTION OF THE INVENTION

Figure 1:
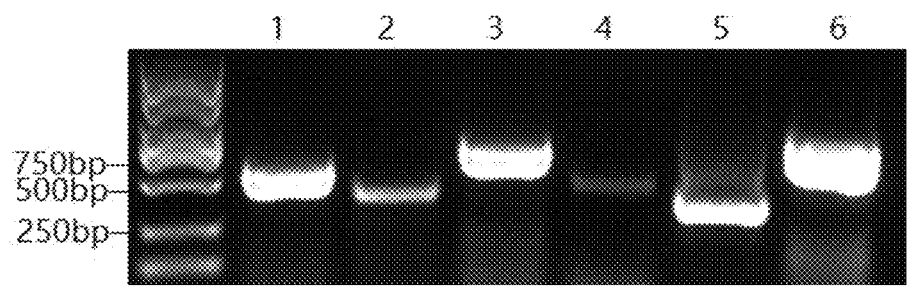
FIG. 1 is a image showing agarose gel electrophoresis results of cDNA of a target gene containing a T7 promoter provided in Example 1 of the present invention, wherein, lanes from left to right are the cDNA of Marker, CP, MP, P126, RdRP2, RdRP3 and RdRP4 genes, which are about 480 bp, 333 bp, 641 bp, 388 bp, 313 bp and 746 bp, respectively, which are consistent with the size of the target gene.

Hereinafter, the technical scheme of the present invention will be clearly and completely described. It is to be understood that the described embodiments are only a few, but not all, embodiments of the invention. Based on the embodiments of the present invention, all other embodiments obtained by a person of ordinary skill in the art without involving any inventive effort are within the scope of the present invention.

Example 1: the embodiment provides a method for screening high-efficiency action fragments and application thereof. After six groups of candidate gene fragments are selected and dsRNA is synthesized in vitro, the antiviral capacity of the candidate gene fragments is evaluated by a biological method, and the dsRNA for efficiently degrading TMV target nucleic acid is screened. The six groups of candidate gene fragments of TMV are CP, MP, P126, RdRP2, RdRP3 and RdRP4, and the gene sequences thereof are as shown in sequences: SEQ ID NOs.4, 5, 6, 7, 1 and 8.

The screening method for dsRNA for efficiently preventing and controlling TMV specifically comprises the following steps of:

S1: extracting total RNA of TMV infected tobacco leaves. Carrying out reverse transcription with the extracted total RNA as a template to obtain cDNA of TMV;

S2: designing specific amplification primers of six sequences of CP, MP, P126, RdRP2, RdRP3 and RdRP4 by taking cDNA as a template, and amplifying a target gene fragment by using the specific primers;

S3: synthesizing dsRNA in vitro by using specific amplification products as templates.

In order to more clearly describe the method for screening highly effective acting fragments provided by the embodiment of the present invention in detail, the following description will be made.

(S1): the total RNA extraction kit is used for extracting the total RNA of the plant leaves, and the specific steps are as follows:

S1-1: collecting fresh tobacco leaves infected with TMV and immediately placing in liquid nitrogen.

S1-2: pre-cooling the mortar by liquid nitrogen until the mortar cannot be held by hands, placing tobacco leaves on the mortar until the tobacco leaves were ground into powder, and continuously adding liquid nitrogen in the mortar.

S1-3: taking 100 mg of the powder into a 1.5 ml centrifuge tube, adding 1 ml RNAiso Plus (Takara) immediately, shaking and uniformly mixing until no macroscopic particles exist, and standing at room temperature for 5 min.

S1-4: centrifuging at 12,000 g, 4° C. for 10 min. Carefully aspirating the supernatant (without aspirating the precipitate) and transferring to a new 1.5 mL centrifuge tube.

S1-5: adding 200 μL chloroform, capping the centrifuge tube, shaking and mixing until being milky white Standing at room temperature for 5 min.

S1-6: centrifuging at 12,000 g, 4° C. for 15 min. The homogenate comprises three layers: the colorless supernatant (containing RNA), the middle white protein layer (mostly DNA), and the colored lower organic phase.

S1-7: carefully aspirating the supernatant (without aspirating the middle white protein layer) and transferring to another new 1.5 mL centrifuge tube.

S1-8: adding 500 μL isopropanol, gently inverting 5 times up and down, and standing at room temperature for 10 min.

S1-9: centrifuging at 12,000 g, 4° C. for 10 min.

S1-10: carefully discarding the supernatant, adding 1 mL 75% ethanol, gently inverting the centrifuging tube, centrifuging at 7,500 g, 4° C. for 5 min, and discarding the supernatant (without touching the precipitate). Repeating once.

S1-11: opening the centrifuge tube cap, drying at room temperature for 5 min, and adding 100 μL RNase-free $H_2O$ to dissolve the precipitate.

Finally, detecting the extracted RNA by 1.0% agarose gel electrophoresis, detection results as shown in FIG. 1, and then storing the extracted RNA in −80° C.

(S2): synthesizing TMV genome cDNA, and in the reaction, carrying out reverse transcription process by utilizing Hiscrit® IIIRT RuperMix for qPCR (+gDNA wiper) kit of Vazyme.

S2-1: thawing 4×gDNA wiper Mix, 5×HiScripT III qRT SuperMix, RNA Template, RNase-Free $H_2O$ on ice, then the following steps were completed on ice;

S2-2: preparing a reaction mixed solution system for removing genome DNA, wherein the specific system comprises: 4×gDNA wiper Mix 4 μl, RNA Template 1 μl (1 μg), RNase-Free $H_2O$ to 16 μl;

S2-3: lightly blowing the pipette and centrifuging for a short time, so that the solution on the tube wall is collected at the bottom of the tube;

S2-4: incubating for 2 min at 42° C.;

S2-5: after the reaction is finished, obtaining a reaction solution I, centrifuging shortly, and cooling on ice;

S2-6: preparing a reverse transcription system mixed solution system, wherein the specific system is: the above reaction solution I 16 μl, 5×HiScript III qRT SuperMix 4 μl;

S2-7: uniformly mixing and centrifuging for a short time, so that the solution on the tube wall is collected at the bottom of the tube;

S2-8: incubating at 37° C. for 15 min, 85° C. for 5 s;

S2-9: after the reaction was complete, storing at −20° C.

(S3): Amplification of Six Genes

S3-1: designing primers of six kinds of genes according to sequence information, the primer sequences are shown in Table 1:

TABLE 1

Gene amplification primers and corresponding sequences

| Gene | Primers | Sequence (5'-3') |
|------|---------|------------------|
| CP | McpP (SEQ ID NO. 9) | 5'-attctctagaagcttaatacgactcact atagggatgtcttacagtatcactactcc |
|  | TMVCP-R (SEQ ID NO. 10) | 5'-attctctagaagcttaatacgactcact atagggagttgcaggaccagagg |
| MP | TMVMP-F (SEQ ID NO. 11) | 5'-attctctagaagcttaatacgactcact ataggggaaagagccgacgag |
|  | TMVMP-R (SEQ ID NO. 12) | 5'-attctctagaagcttaatacgactcact ataggggcaagcctgattgacata |
| P126 | TMVP/26-P (SEQ ID NO. 13) | 5'-attctctagaagcttaatacgactcact atagggtcttaccgtcgatgttt |
|  | TMVP126-R (SEQ ID NO. 14) | 5'-attctctagaagcttaatacgactcact ataggggttcttgttcggcact |
| RdRP2 | TMVRdRP-F (SEQ ID NO. 15) | 5'-attctctagaagcttaatacgactcact atagggcttacttcccggcctcta |
|  | TMRdRP-R (SEQ ID NO. 16) | 5'-attctctagaagcttaatacgactcact ataggggctttcgcctggtatgtt |
| RdRP3 | TMVRdRP-F (SEQ ID NO. 2) | 5'-attctctagaagcttaatacgactcact atagggatttcgctggcgtttg |
|  | TMVRARP-R (SEQ ID NO. 3) | 5'-attctctagaagcttaatacgactcact atagggctgccgtcattgggtc |
| RdRP4 | TMWRF-F (SEQ ID NO. 17) | 5'-attctctagaagcttaatacgactcact atagggtgaccttccacgacaga |
|  | TMRdRP-R (SEQ ID NO. 18) | 5'-attctctagaagcttaatacgactcact atagggagcgccacatgatactt |
| actin | actin-F (SEQ ID NO. 19) | 5'-caaggaaatcaccgctttgg |
|  | actin-R (SEQ ID NO. 20) | 5'-aagggatgcgaggatgga |
| TMV | TMV-F (SEQ ID NO. 21) | 5'-caaggaaatcaccgctttgg |
|  | TMV-R (SEQ ID NO. 22) | 5'-aagggatgcgaggatgga |

S3-2: carrying out a PCR amplification reaction on the TMV genome with cDNA as a template by using primers specifically containing a T7 promoter as shown in table 1 to obtain amplification products of TMV CP, MP, P126, RdRP2, RdRP3 and RdRP4 genes containing the T7 promoter; in the reaction, carrying out reverse transcription process by utilizing Hiscrit® IIIRT SuperMix for qPCR (+gDNA wiper) kit of Vazyme.

The PCR reaction system specifically comprises: 2×Phanta Max Master Mix 25 μl; template DNA 1 μl; primer F 2 μl; primer R 2 μl; $H_2O$ to 50 μl;

PCR amplification conditions are as follows: pre-denaturing for 3 min at 95° C.; denaturing for 15 s at 95° C., annealing for 30 s at $T_m$, extending for 30 s at 72° C., a total of 35 cycles; final extending for 5 min at 72° C., at last insulating at 8° C.

(S4): preparing dsRNA of six kinds of genes through in-vitro transcription, and carrying out in-vitro transcription preparation according to instructions of an In vitro Transcription T7 Kit (for siRNA Synthesis) kit of TaKaRa, and the specific operations are as follows:

S4-1: preparation of dsRNA: preparing a 40 μl reaction system by taking 15 μl PCR amplification products, wherein the reaction system is as follows: 10× Transcription Buffer 4 μl, ATP Solution 4 GTP Solution 4 μl, CTP Solution 4 μl, UTP Solution 4 μl, RNase Inhibitor 1 μl, T7 RNA Polymerase 4 μl and linear template DNA 15 μl;

S4-2: uniformly mixing the solution, slightly centrifuging, collecting the transcription reaction solution at the bottom of a reaction tube, and reacting at 42° C. for 2 hours;

S4-3: adding 6 μl RNase free DNase I into the above solution after the transcription reaction, and uniformly mixing;

S4-4: reacting at 37° C. for 30 min.

S4-5: purifying dsRNA: when the reaction liquid volume was 40 μl, adding 60 μl RNase free $H_2O$ to make up to 100 μl.

(1) adding an equal volume of phenol (pH 4.5)/chloroform/isoamyl alcohol (25:24:1), stirring well and centrifuging at 12,000 rpm for 2 min at room temperature.

(2) transferring the upper layer (aqueous layer) to a new centrifuge tube and adding an equal volume of chloroform/isoamyl alcohol (24:1), stirring and centrifuging at 12,000 rpm for 2 min at room temperature.

(3) transferring the upper layer (aqueous layer) to a new centrifuge tube and adding 1/10 volume of 3 M glacial sodium acetate, an equal volume of isopropanol and mixing well.

(4) standing for 5 min at room temperature, centrifuging at 15,000 rpm for 5 min at room temperature.

(5) removing the supernatant and washing the precipitate with 80% ethanol.

(6) adding 40 μl A RNase free $H_2O$ after drying to dissolve the precipitate and storing at −20° C.

Figure 2:
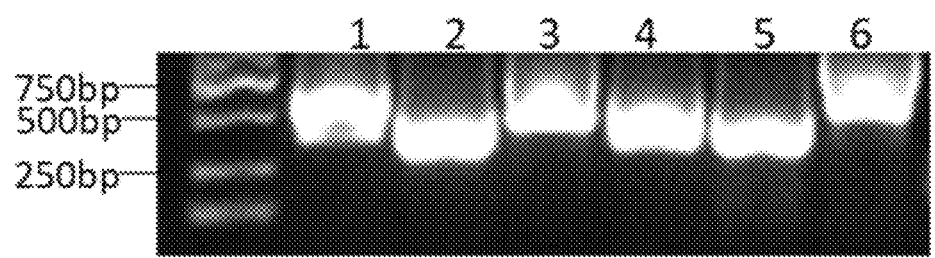
FIG. 2 is a image of agarose gel electrophoresis results of in vitro transcriptionally synthesized dsRNA provided in Example 1 of the present invention, wherein, lanes from left to right are Marker, CP dsRNA, MP dsRNA, P126 dsRNA, RdRP2 dsRNA, RdRP3 dsRNA and RdRP4 dsRNA, respectively.

S4-6: detection of dsRNA: taking 2 μl dsRNA product to mix with 6× loading buffer and detecting by agarose gel electrophoresis, observing whether the bands are single and bright or not, and the electrophoresis detection result is shown in FIG. 2; determining the concentration of dsRNA by using a micro-spectrophotometer.

(S5) screening of highly effective disease-resistant specific dsRNA.

S5-1: plantation and transplantation of laboratory tobacco: scattering a *nicotiana* benthamian seed in a tray and covering a film, transferring tobacco seedlings to a disposable plastic cup after seeds germinating for about one week and growing to the size suitable for transplanting, culturing for about one month, and growing tobacco plants to the size suitable for processing.

S5-2: injection of dsRNA with inoculation of TMV: the method of injecting dsRNA first and inoculating TMV virus 24 h later was adopted in this experiment. Selecting uniformly-sized *nicotiana* benthamian leaves in advance, and marking Dissolving 200 μg dsRNA in 0.7 ml $H_2O$ and injecting into the leaves, but injecting only 0.7 ml $H_2O$ into the control leaves. 24 h later, inoculating virus, weighing a small amount of TMV poison source leaves, grinding into juice in a mortar, adding 100 times of volume of PBS buffer solution (pH 6.8) and uniformly mixing, scattering a layer of 100-mesh quartz sand on uniformly-sized *nicotiana* benthamian leaves, dipping the poison source juice with a cotton swab to lightly spread on the leaves to cause micro wounds to infect viruses, and ensuring consistent virus inoculation amount and uniform force as far as possible. 24 h, 48 h and 72 h after virus inoculation, cutting the inoculated leaves and freezing in liquid nitrogen respectively, three biological replicates were taken every day and storing at −80° C. for real-time RT-PCR and Western Blot.

S5-3: extracting RNA from the sample leaves for real-time RT-PCR.

mRNA relative expression level of Actin was measured by Actin-F/R and mRNA relative expression level of TMV CP were measured by TMV-F/R. Primer sequences are shown in Table 1. Carrying out the real-time RT-PCR according to the instruction of the ChamQ™ Universal SYBR qPCR Master Mix kit of Vazyme, and the specific operation was as follows:

(1) obtaining cDNA: obtaining cDNA from dsRNA of $H_2O$, CP, MP, P126, RdRP2, RdRP3 and RdRP4-treated infected leaves with reference to S1 and S2 of embodiment 1.

(2) taking a 96-well reaction plate MicroAmp Fast Optical 96-Well Reaction Plate with Barcode (ABI), and configuring a real-time RT-PCR system, wherein the specific system is as follows: 2×ChamQ Universal SYBR qPCR Master Mix 10 μl, Primer F 0.4 μl; primer R 0.4 μl; cDNA 1 μl, $H_2O$ 8.2 μl.

(3) lightly flipping tube wall, uniformly mixing, and centrifuging shortly by using a 96-hole reaction plate to avoid bubbles.

Figure 3:
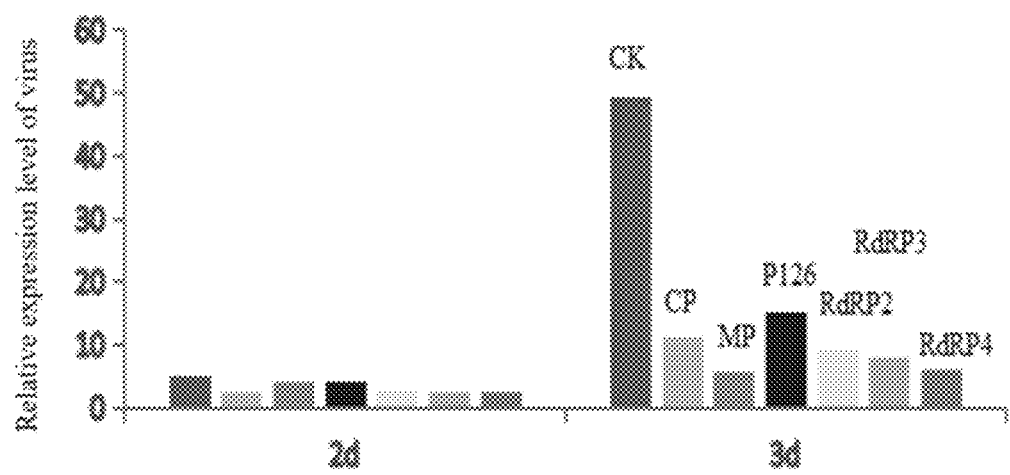
FIG. 3 is a graph showing the effect of different dsRNA treatments on the expression level of wild-type TMV.

(4) finishing real-time RT-PCR reaction in an Applied Biosystems 7500 Fast Real-Time PCR System. The reaction procedure was 95° C. for 30 s; 95° C. for 10 s, 60° C. for 30 s, 40 cycles; 95° C. for 15 s, 60° C. for 1 min, 95° C. for 15 s, the reaction was completed and the results were analyzed. The results are shown in FIG. 3, from which it can be seen that: on the third day, the relative expression of virus in the plants treated by MP, RdRP3 and RdRP4 was lower, and the antiviral effect was more obvious.

S5-4: extracting total protein from the sample leaves. Using the Plant Protein Extraction Kit reagent of Cowin Bio. to extract protein from sample leaves, and the specific operation is as follows:

(1) taking out the Plant Protein Extraction Reagent required by the experiment before protein extraction for precooling.

(2) weighing the test plant tissue. Adding 5 ml of Plant Protein Extraction Reagent (adding Protease Inhibitor Cocktail added at a ratio of 1:99 before protein extraction) to 1 g tissue.

(3) incubating on ice for 30 min after homogenization.

(4) at 4° C. 13,400×g, centrifuging for 20 min.

(5) collecting soluble proteins in the supernatant and storing at −80° C. ready for further analysis.

S5-5: Western Blot detection.

(1) taking supernatant protein solution 8 μl for mixing and adding 2×SDS loading buffer with equal volume of 8 μl into PCR tube. After boiling in boiling water for 5 min, loading 15 μL six kinds of treated protein CP, MP, P126, RdRP2, RdRP3 and RdRP4 into sample well respectively, adding 8 μL Blue Plus II protein maker into sample well. Carrying out electrophoresis at 180 V for 35 min until the loading buffer dye was transferred to the bottom of the gel.

(2) removing the glass plate and pry it with a doctor-bar, removing the gel, removing the stacking gel, and soaking the separation gel in the transfer buffer.

(3) soaking the sponge pad and the thick filter paper with a transfer buffer, cutting a PVDF membrane with proper size, soaking in methanol for 10 s, sequentially installing the sponge pad, the thick filter paper, the separation gel and the PVDF membrane, and removing bubbles between the separation gel and the PVDF membrane. Putting an ice boxes in the transfer buffer and transferring membranes at 100 V for 90 min.

(4) after finishing the membrane transfer, dyeing the separation gel with a Coomassie brilliant blue protein gel fast dyeing solution, decoloring and taking photo by using a chemiluminescence imager.

(5) washing the PVDF membrane three times with TBST buffer for 10 min each time.

(6) blocking PVDF membranes in blocking solution (0.5 g BSA in 10 mL TB ST) at 45 rpm for 1 h at room temperature.

(7) taking PVDF membrane out and placing in TB ST containing primary antibody (diluted 2000-fold, Abcam) at 4° C. overnight.

(8) washing the PVDF membrane three times with TB ST for 10 min each time.

(9) placing in TB ST containing secondary antibody (diluted 5000-fold, Abcam), shaking at 45 rpm for 1 h.

(10) washing the PVDF membrane three times in TBST for 10 min each time.

Figure 4:
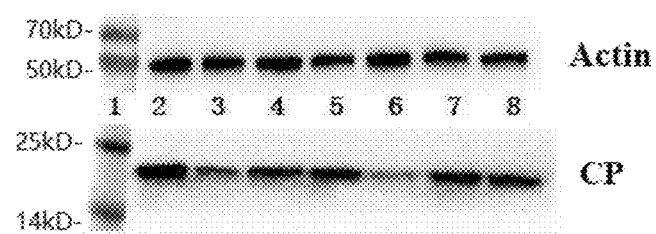
FIG. 4 shows the results of Western Blot on tobacco leaves after dsRNA treatment for each group.

(11) preparing a luminescent liquid by using an eECL Western Blot Kit, smearing on a membrane, and taking photo by using a chemiluminescence imager. The results of Western Blot on tobacco leaves after dsRNA treatment for each group are shown in FIG. 4. The results of Western Blot showed that the expression level of CP protein of TMV virus decreased in different degrees after injection of dsRNA, which indicated that dsRNA could inhibit the replication and infection of TMV.

Example 2: the application of the high-efficiency dsRNA further screened in Example 1 in the prevention of TMV virus, the specific application methods are as follows:

S1: planting and transplanting laboratory tobacco: procedure referring to S5-1 of Example 1, growing tobacco plants an appropriate size.

S2: injection of dsRNA with inoculation of TMV-30b: the method of injecting dsRNA first and inoculating TMV-30b virus 24 h later was adopted in this experiment. Selecting uniformly-sized *nicotiana* benthamian leaves in advance, and marking Dissolving 200 µl dsRNA of MP, RdRP3 in 0.7 ml H$_2$O and injecting into the leaves, but injecting only 0.7 ml H$_2$O into the control leaves. 24 h later, inoculating virus, weighing a small amount of TMV-30b poison source leaves, grinding into juice in a mortar, adding 40 times of volume of PBS buffer solution (pH 6.8) and uniformly mixing, scattering a layer of 100-mesh quartz sand on uniformly-sized *nicotiana* benthamian leaves, dipping the poison source juice with a cotton swab to lightly spread on the leaves to cause micro wounds to infect viruses, and ensuring consistent virus inoculation amount and uniform force as far as possible. 3 d and 5 d after virus inoculation, observing fluorescence and taking photos under ultraviolet light, cutting the inoculated leaves and freezing in liquid nitrogen respectively, three biological replicates were taken every day and storing at −80° C. for real-time RT-PCR.

Figure 5:
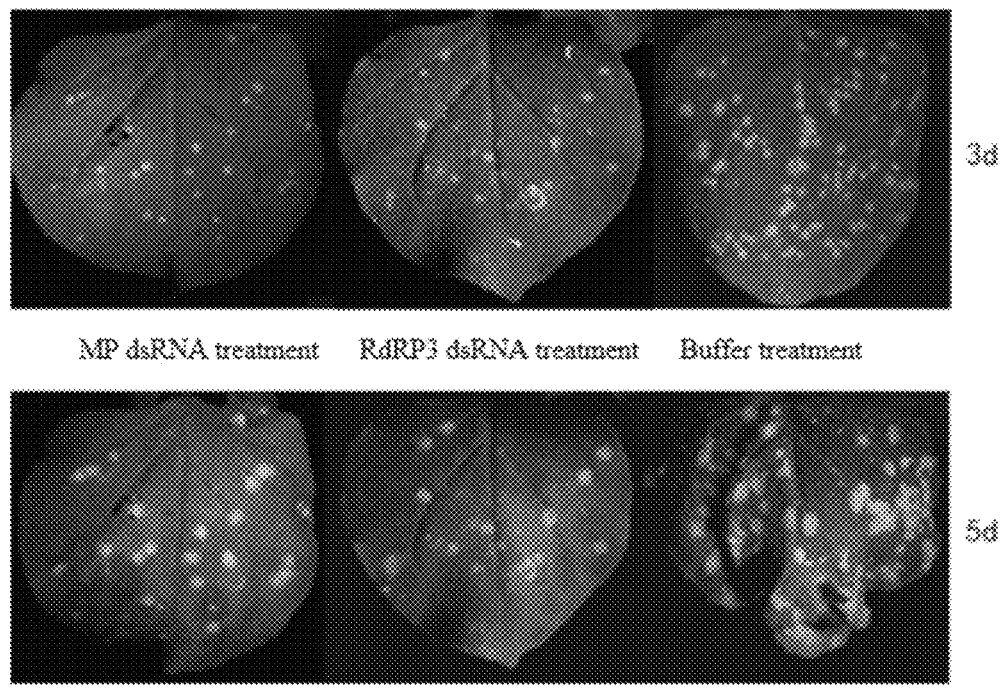
FIG. 5 is a photograph of real-time fluorescence quantitative detection 3d and 5d after exposure of tobacco leaves to virus.
Figure 6:
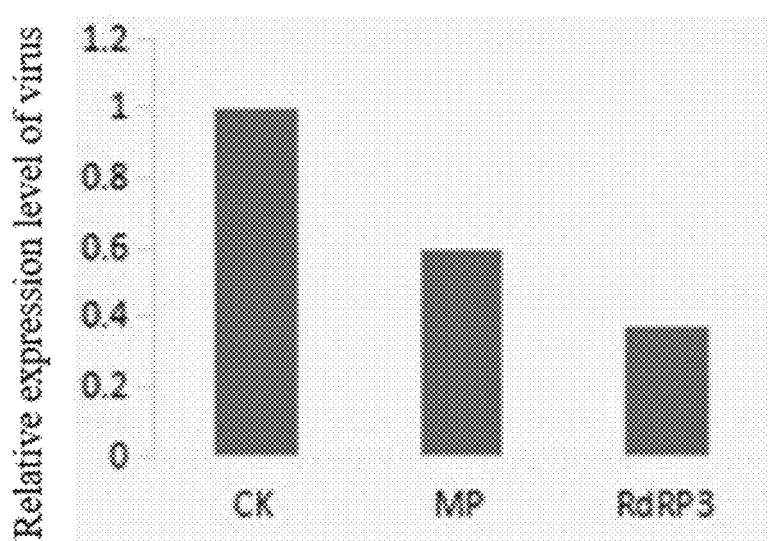
FIG. 6 shows the effect of different dsRNA treatments for 5 days on TMV-30b expression level.

S3: real-time RT-PCR procedure referring to S5-3 of Example 1, carrying out fluorescent quantitative detection. Fluorescence photos are shown in FIG. 5, from which it can be seen that the leaves of *nicotiana* benthamian treated with RdRP3 dsRNA have less fluorescence and can significantly prolong the withering time of the leaves. The effect of different dsRNA treatments for 5 days on the expression level of TMV-30b, the experimental results are shown in FIG. 6, it can be seen from the figure that the virus expression level of RdRP3 on the fifth day is lower, and the antiviral effect is relatively more obvious. In combination with the above experimental results, RdRP3 was finally selected as the target dsRNA.

In order to more clearly describe the RNAi nano-preparation for TMV prevention and control and the preparation method thereof provided by the present invention, a description will be given below with reference to specific examples.

Example 3: a preparation method of the nano RNAi preparation for TMV prevention and control, comprises the following steps:

(S1) binding the chitosan nano material with dsRNA, the specific operation steps are as follows:

S1-1: dissolving chitosan in glacial acetic acid to prepare a chitosan solution A with a final concentration of 2 µg/µl;

S1-2: slowly adding a TMV dsRNA solution with the concentration of 1 µg/µl into a chitosan solution A, wherein the volume ratio of chitosan to dsRNA is 10:(1-6). If the mass ratio is too low, many dsRNA will not bind to chitosan, so that the prevention and control effect of TMV virus is finally influenced, and if the ratio is too high, many chitosan nano materials are not attached with dsRNA, resulting in unnecessary waste.

Figure 7:
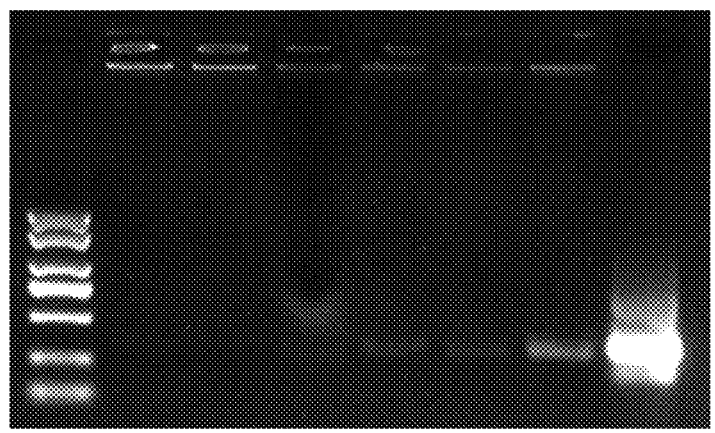
FIG. 7 is an agarose gel electrophoresis image of dsRNA provided by the invention fused with chitosan in different proportions, wherein: lanes from left to right are Marker, RdRP3 dsRNA, respectively: chitosan 1:2, 1:5, 1:10, 1:20, 1:30, 1:40, RdRP3 dsRNA.

The dsRNA of the RdRP3 gene is respectively provided with six mixing ratios, the volume ratio of chitosan glacial acetic acid solution:dsRNA was 10:1, 10:2, 10:3, 10:4, 10:5 and 10:6, respectively;

S1-3: mixing a chitosan solution of dsRNA and a 1% SDS solution in a volume ratio of 2:1, and performing vortex shaking for 5 min;

S1-4: 5 µl mixed solution was added to 1 µl 6×DNA loading buffer, and observing the results after agarose gel electrophoresis. If no bands were present and bright bands appeared around the wells, it was confirmed that the chitosan dsRNA was stable and successfully bound, and the results of fusion of dsRNA with different chitosans are shown in FIG. 7.

Figure 8:
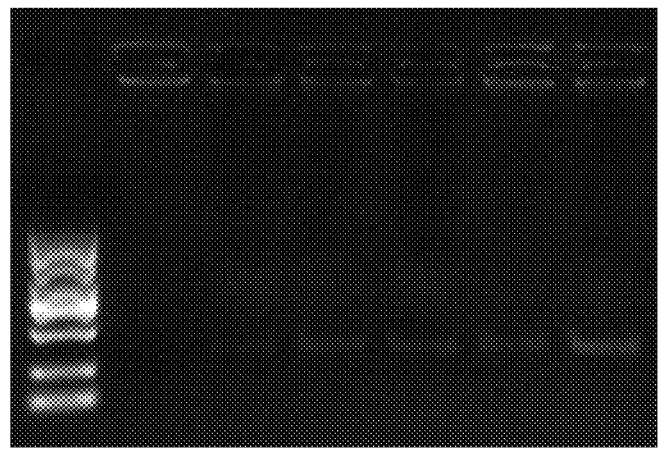
FIG. 8 is an agarose gel electrophoresis image of a nano-preparation provided in the present invention after 10 d of storage, wherein, lanes from left to right are Marker, RdRP3 dsRNA, respectively: chitosan 1:2, 1:5, 1:10, 1:20, 1:30, 1:40.

S1-5: keeping the nano-preparations of dsRNA fused with chitosan with different proportions at room temperature for 10 d, taking 5 µl mixed solution to add into 1 µl 6×DNA loading buffer, and the agarose gel electrophoresis observation results are shown in FIG. 8, testing the stability of the preparations. As shown in the figure, the electrophoresis results are similar to those of S1-4, indicating that the nano-preparation is strong in stability and not easy to degrade.

Wherein: the concentration of dsRNA is 1-2 µg/µl; the concentration of dsRNA is preferably: 1, 1.5, 2 µg/µl, etc.

The RNAi nano-preparation is prepared from dsRNA and chitosan nano materials, the dsRNA is prepared from RNA-dependent RNA polymerase, namely RdRP3 gene, and the gene plays a key role in TMV replication in plants. The specific silencing of the functional gene by RNAi technology is significant for the prevention and control of TMV virus.

Example 4: the application of the prepared RNAi nano-preparation, the method of use is to uniformly smear or spray the finished solution on the plant leaves. The specific application method comprises the following steps:

S1: plantation and transplantation of laboratory tobacco: scattering a tobacum samsan seed in a tray and covering a film, transferring tobacco seedlings to a disposable plastic cup after seeds germinating for about one week and growing to the size suitable for transplanting, culturing for about one month, and growing tobacco plants to the size suitable for processing.

Figure 9:
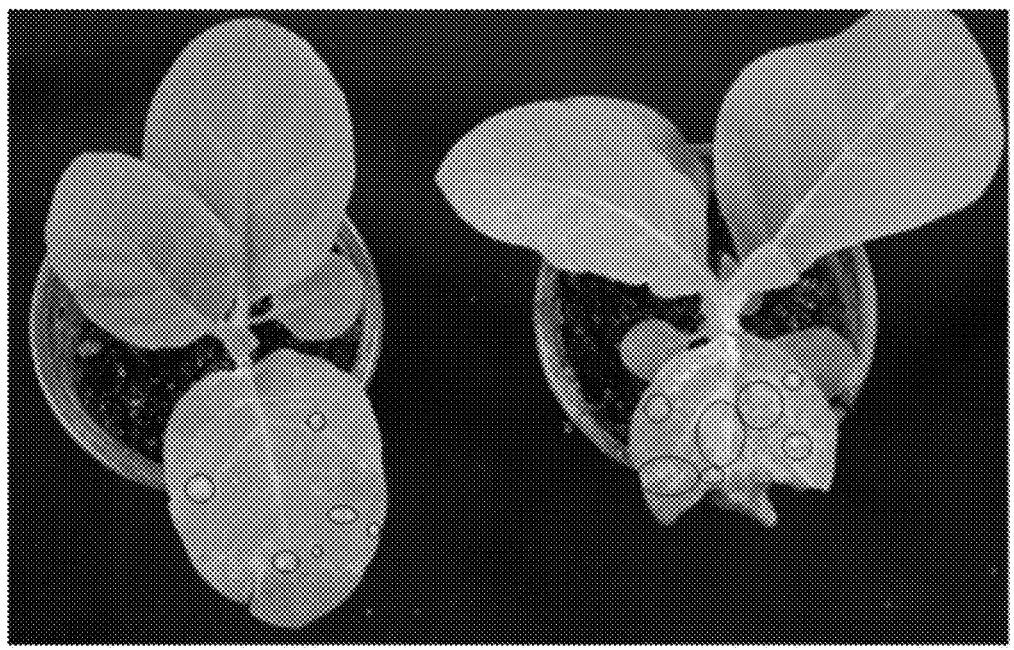
FIG. 9 is a photograph showing necrotic lesion of tobacum samsan after being sprayed with the nano-preparation provided by the invention for 3 d.

S2: spraying nano medicine and inoculating wild type TMV: in this experiment, the wild type TMV virus was inoculated 12 h after spraying the drug. Selecting uniformly-sized tobacum samsan leaves in advance, and marking. The nano-drugs were uniformly sprayed on the leaves, and only H$_2$O was sprayed on the leaves of the control group. 12 h later, inoculating virus, weighing a small amount of wild type TMV poison source leaves, grinding into juice in a mortar, adding 100 times of volume of PBS buffer solution (pH 6.8) and uniformly mixing, scattering a layer of 100-mesh quartz sand on uniformly-sized tobacum samsan leaves, dipping the poison source juice with a cotton swab to lightly spread on the leaves to cause micro wounds to infect viruses, and ensuring consistent virus inoculation amount and uniform force as far as possible. After 3 d of virus inoculation, the number of necrotic lesions was observed and photographed. As shown in FIG. 9, only a small number of necrotic lesion appeared on the leaves of the tobacco plants treated with the nano-drug, while a large number of necrotic lesion appeared on the leaves of the tobacco plants treated with the water in the control group and the symptoms of wilting appeared, indicating that the efficacy of the nano-drug is obvious.

SEQUENCE LISTING

<110> Tobacco Research Institute of Chinese Academy of Agricultural Sciences; Sichuan Brunch of China Tobacco; Liangshan Branch of Sichuan Tobacco
<120> RNAi nano-preparation, preparation method thereof and application thereof in TMV prevention and control
<130> U.S. Ser. No. 16/998,957
<140> U.S. Ser. No. 16/998,957
<141> 2020-08-20
<160> 22
<170> PatentIn version 3.5
<210> 1
<211> 313
<212> DNA
<213> Artificial Sequence
<220>
<223> Synthesized
<400> 1
atttcgctgg cgtttgggaa cgcatttccc tccgtgaaag agaggctctt gaacaggaaa 60
cttatcagag tggcaggcga cgcattagag atcagggtgc ctgatctata tgtgaccttc 120
cacgacagat tagtgactga gtacaaggcc tctgtggaca tgcctgcgct tgacattagg 180
aagaagatgg aagaaacgga agtgatgtac aatgcacttt cagagttatc ggtgttaagg 240
gagtctgaca aatttgatgt tgatgttttt tcccagatgt gccaatatt ggaagttgac 300
ccaatgacgg cag 313
<210> 2
<211> 50
<212> DNA
<213> Artificial Sequence
<220>
<223> Synthesized
<400> 2
attctctaga agcttaatac gactcactat agggatttcg ctggcgtttg 50
<210> 3
<211> 50
<212> DNA
<2137> Artificial Sequence
<220>
<223> Synthesized
<400> 3
attctctaga agcttaatac gactcactat agggctgccg tcattgggtc 50
<210> 4
<211> 477
<212> DNA
<213> Artificial Sequence
<220>
<223> Synthesized
<400> 4
atgtcttaca gtatcactac tccatctcag ttcgtgttct tgtcatcagc gtgggccgac 60
ccaatagagt taattaattt: atgtactaat gctttaggaa atcagtttca aacacaacaa 120
gctcgaactg tcgttcaaag acaattcagt gaggtgtgga aaccttcacc acaagtaact 180
gttaggttcc ctgacagtga ctttaaggtg tacaggtaca atgcggtatt agacccgcta 240
gtcacagcac tgttaggtgc attcgacact agaaatagaa taatagaagt tgaaaatcag 300
gcgaacccca cgactgccga aacgttagat gctactcgta gagtagacga cgcaacggtg 360
gccataagga gcgcgataaa taatttaata gtagaattga tcagaggaac cggatcttat 420
aatcggagct ctttcgagag ctcttctggt ttggtttgga cctctggtcc tgcaact 477
<210> 5
<211> 333
<212> DNA
<213> Artificial Sequence
<220>
<223> Synthesized
<400> 5
ggaaagagcc gacgaggcca cictcggatc ttactacaca gcagctgcaa agaaaagatt: 60
tcagttcaag gtcgttccca attatgctat aaccacccag gacgcgatga aaaacgtctg 120
gcaagtttta gttaatatta gaaatgtgaa gatgtcagcg ggtttctgtc cgctttctct 180
ggagtttgtg tcggtgtgta ttgtttatag aaataatata aaattaggtt tgagagagaa 240
gattacaaac gtgagagacg gagggccc it ggaacttaca gaagaagtcg ttgatgagtt 300
catggaagat gtccctatgt caatcaggct tgc 333
<210> 6
<211> 641
<212> DNA
<213> Artificial Sequence
<220>
<223> Synthesized
<400> 6
tcttaccgtc gatgtnacc cctgtaaaga gtgttatgtg ttccaaagtt gataaaataa 60
tggttcatga gaatgagtca ngtcagagg tgaaccttct taaaggagtt aagcttaag 120
atagtggata cgtctgtita gccggtttgg tcgtcacggg cgaatggaac ngcctgaca 180
attgcagagg aggtgtgagc gtgtgtctgg tggacaaaag gatggaaaga gccgacgagg 240
ccactctcgg atcttactac acagcagctg caaagaaaag atttcagttc aaggtcgttc 300
ccaattatgc tataaccacc caggacgcga tgaaaaacgt ctggcaagtt ttagttaata 360
ttagaaatgt gaagatgtca gcgggtttct gtccgctttc tctgg agttt gtgtcggtgt 420
gtattgttta tagaaataat ataaaattag gtttgagaga gaagattaca aacgtgagag 480
acggagggcc catgaactt acagaagaag tcgttgatga gttcatggaa gatgtcccta 540
tgtcaatcag gcttgcaaag tttcgatctc ggaccggaaa aaagagtgat gtccgtaaag 600
ggaaaaatag tagtagtgat cggtcagtgc cgaacaagaa c 641
<210> 7
<211> 388
<212> DNA
<213> Artificial Sequence
<220>
<223> Synthesized
<400> 7
cttacttccc ggcctctaat agagaggttt acatgaagga gttttagtc accagagtta 60 atacctggtt ttgtaagttt tctagaatag atactttct tttgtacaaa
ggtgtggccc 120
ataaaagtgt agatagtgag cagtttata ctgcaatgga agacgcgtgg cat-
tacaaaa 180
agactcttgc aatgtgcaac agcgagagaa tcctccttga ggattcatca
tcagtcaatt 240
actggtttcc caaaatgagg gatatggtca tcgtaccatt attcgacatt tctttg-
gaga 300
ctagtaagag gacgcgcaag gaagtcttag tgtccaagga tttcgtgttt
acagtgctta 360
accacattcg aacataccag gcgaaagc 388
<210> 8
<211> 757
<212> DNA
<213> Artificial Sequence
<220>
<223> Synthesized
<400> 8
tgaccttcca cgacagatta gtgactgagt acaaggcctc tgtggacatg
cctgcgcttg 60
acattaggaa gaagatggaa gaaacggaag tgatgtacaa tgcactttca
gagttatcgg 120
tgttaaggga gtctgacaaa tttgatgttg atgttttttc ccagatgtgc
caatctttgg 180
aagttgaccc aatgacggca gcgaaggtta tagtcgcggn catgagcaat
gagagcggtc 240
tgactctcac ttttgaacga cctactgagg cgaatgttgc gctagcttta cag-
gatcaag 300
agaaggcttc agaaggtgct ttggtagtta cctcaagaga agtgaagaa
ccgtccatga 360
agggttcgat ggccagagga gagttacaat tagctggtct tgctggagat
catccggagt 420
cgtcctattc taagaacgag gagatagagt ctttagagca gtttcatatg
gcaacggcag 480
attcgttaat tcgtaagcag atgβgctcga ttgtgtacac gggtccgatt
aaagttcagc 540
aaatgaaaaa ctttatcgat agcctggtag catcactatc tgctgcggtg
tcgaatctcg 600
tcaagatcct caaagataca gctgctattg accttgaaac ccgtcaaaag tttg-
gagtct 660
tgfatgttgc atctaggaag tggttaatca aaccaacggc caagagtcat
gcatggggtg 720
ttgttgaaac ccacgcgagg aagtatcatg tggcgct 757
<210> 9
<211> 57
<212> DNA
<213> Artificial Sequence
<220>
<223> Synthesized
<400> 9
attctctaga agcttaatac gactcactat agggatgtct tacagtatca ctactcc
57
<210> 10
<211> 51
<212> DNA
<2137> Artificial Sequence
<220>
<223> Synthesized
<400> 10
attctctaga agcttaatac gactcactat agggagttgc aggaccagag g 51
<210> 11
<211> 50
<212> DNA
<213> Artificial Sequence
<220>
<223> Synthesized
<400> 11
attctctaga agcttaatac gactcactat agggggaaag agccgacgag 50
<210> 12
<211> 52
<212> DNA
<213> Artificial Sequence
<220>
<223> Synthesized
<400> 12
attctctaga agcttaatac gactcactat aggggcaagc ctgattgaca ta 52
<210> 13
<211> 51
<212> DNA
<213> Artificial Sequence
<220>
<223> Synthesized
<400> 13
attctctaga agcttaatac gactcactat agggtcttac cgtcgatgtt t 51
<210> 14
<211> 50
<212> DNA
<213> Artificial Sequence
<220>
<223> Synthesized
<400> 14
attctctaga agcttaatac gactcactat aggggttctt gttcggcact 50
<210> 15
<211> 52
<212> DNA
<213> Artificial Sequence
<220>
<223> Synthesized
<400>15
attctctaga agcttaatac gactcactat agggcttact tcccggcctc to 52
<210> 16
<211> 52
<212> DNA
<2137> Artificial Sequence
<220>
<223> Synthesized
<400>16
attctctaga agcttaatac gactcactat aggggctttc gcctggtatg tt 52
<210> 17
<211> 51
<212> DNA
<213> Artificial Sequence
<220>
<223> Synthesized
<400> 17
attctaga agcttaatac gactcactat agggtgacct tccacgacag a 51
<210>18
<211>51
<212> DNA
<213> Artificial Sequence
<220>
<223> Synthesized
<400> 18
attctctaga agcttaatac gactcactat agggagcgcc acatgatact t 51
<210> 19
<211> 20
<212> DNA
<213> Artificial Sequence
<220>
<223> Synthesized
<400> 19
caaggaaatc accgctttgg 20

| | |
|---|---|
| <110> 20 | <220> |
| <211> 18 | <223> Synthesized |
| <212> DNA | <400> 21 |
| <213> Artificial Sequence | caaggaaatc accgctttgg 20 |
| <220> | <210> 22 |
| <223> Synthesized | <211> 113 |
| <400> 20 | <212> DNA |
| aagggatgcg aggatgga 18 | <213> Artificial Sequence |
| <210> 21 | <220> |
| <211> 20 | <223> Synthesized |
| <212> DNA | <400> 22 |
| <213> Artificial Sequence | aagggatgcg aggatgga 18 |

```
                         SEQUENCE LISTING

<160> NUMBER OF SEQ ID NOS: 22

<210> SEQ ID NO 1
<211> LENGTH: 313
<212> TYPE: DNA
<213> ORGANISM: Artificial Sequence
<220> FEATURE:
<223> OTHER INFORMATION: Synthesized

<400> SEQUENCE: 1
atttcgctgg cgtttgggaa cgcatttccc tccgtgaaag agaggctctt gaacaggaaa      60
cttatcagag tggcaggcga cgcattagag atcagggtgc ctgatctata tgtgaccttc     120
cacgacagat tagtgactga gtacaaggcc tctgtggaca tgcctgcgct tgacattagg     180
aagaagatgg aagaaacgga agtgatgtac aatgcacttt cagagttatc ggtgttaagg     240
gagtctgaca aatttgatgt tgatgttttt tcccagatgt gccaatcttt ggaagttgac     300
ccaatgacgg cag                                                       313

<210> SEQ ID NO 2
<211> LENGTH: 50
<212> TYPE: DNA
<213> ORGANISM: Artificial Sequence
<220> FEATURE:
<223> OTHER INFORMATION: Synthesized

<400> SEQUENCE: 2
attctctaga agcttaatac gactcactat agggatttcg ctggcgtttg                 50

<210> SEQ ID NO 3
<211> LENGTH: 50
<212> TYPE: DNA
<213> ORGANISM: Artificial Sequence
<220> FEATURE:
<223> OTHER INFORMATION: Synthesized

<400> SEQUENCE: 3
attctctaga agcttaatac gactcactat agggctgccg tcattgggtc                 50

<210> SEQ ID NO 4
<211> LENGTH: 477
<212> TYPE: DNA
<213> ORGANISM: Artificial Sequence
<220> FEATURE:
<223> OTHER INFORMATION: Synthesized

<400> SEQUENCE: 4
atgtcttaca gtatcactac tccatctcag ttcgtgttct tgtcatcagc gtgggccgac      60
ccaatagagt taattaattt atgtactaat gctttaggaa atcagtttca aacacaacaa     120
gctcgaactg tcgttcaaag acaattcagt gaggtgtgga aaccttcacc acaagtaact     180
```

```
gttaggttcc ctgacagtga ctttaaggtg tacaggtaca atgcggtatt agacccgcta    240
gtcacagcac tgttaggtgc attcgacact agaaatagaa taatagaagt tgaaaatcag    300
gcgaacccca cgactgccga aacgttagat gctactcgta gagtagacga cgcaacggtg    360
gccataagga gcgcgataaa taatttaata gtagaattga tcagaggaac cggatcttat    420
aatcggagct ctttcgagag ctcttctggt ttggtttgga cctctggtcc tgcaact      477

<210> SEQ ID NO 5
<211> LENGTH: 333
<212> TYPE: DNA
<213> ORGANISM: Artificial Sequence
<220> FEATURE:
<223> OTHER INFORMATION: Synthesized

<400> SEQUENCE: 5
ggaaagagcc gacgaggcca ctctcggatc ttactacaca gcagctgcaa agaaaagatt    60
tcagttcaag gtcgttccca attatgctat aaccacccag gacgcgatga aaacgtctg    120 gcaagtttta gttaatatta gaaatgtgaa gatgtcagcg ggtttctgtc cgctttctct    180
ggagtttgtg tcggtgtgta ttgtttatag aaataatata aaattaggtt tgagagagaa    240
gattacaaac gtgagagacg gagggcccat ggaacttaca gaagaagtcg ttgatgagtt    300
catggaagat gtccctatgt caatcaggct tgc                                333

<210> SEQ ID NO 6
<211> LENGTH: 641
<212> TYPE: DNA
<213> ORGANISM: Artificial Sequence
<220> FEATURE:
<223> OTHER INFORMATION: Synthesized

<400> SEQUENCE: 6
tcttaccgtc gatgtttacc cctgtaaaga gtgttatgtg ttccaaagtt gataaaataa    60
tggttcatga gaatgagtca ttgtcagagg tgaaccttct taaaggagtt aagcttattg    120
atagtggata cgtctgttta gccggtttgg tcgtcacggg cgaatggaac ttgcctgaca    180
attgcagagg aggtgtgagc gtgtgtctgg tggacaaaag gatggaaaga gccgacgagg    240
ccactctcgg atcttactac acagcagctg caaagaaaag atttcagttc aaggtcgttc    300
ccaattatgc tataaccacc caggacgcga tgaaaaacgt ctggcaagtt ttagttaata    360
ttagaaatgt gaagatgtca gcgggtttct gtccgctttc tctggagttt gtgtcggtgt    420
gtattgttta tagaaataat ataaaattag gtttgagaga gaagattaca aacgtgagag    480
acggagggcc catggaactt acagaagaag tcgttgatga gttcatggaa gatgtcccta    540
tgtcaatcag gcttgcaaag tttcgatctc ggaccggaaa aaagagtgat gtccgtaaag    600
ggaaaaatag tagtagtgat cggtcagtgc cgaacaagaa c                       641

<210> SEQ ID NO 7
<211> LENGTH: 388
<212> TYPE: DNA
<213> ORGANISM: Artificial Sequence
<220> FEATURE:
<223> OTHER INFORMATION: Synthesized

<400> SEQUENCE: 7
cttacttccc ggcctctaat agagaggttt acatgaagga gttttagtc accagagtta    60 atacctggtt ttgtaagttt tctagaatag atactttct tttgtacaaa ggtgtggccc    120
```

```
ataaaagtgt agatagtgag cagttttata ctgcaatgga agacgcgtgg cattacaaaa        180
agactcttgc aatgtgcaac agcgagagaa tcctccttga ggattcatca tcagtcaatt        240
actggtttcc caaaatgagg gatatggtca tcgtaccatt attcgacatt tctttggaga        300
ctagtaagag gacgcgcaag gaagtcttag tgtccaagga tttcgtgttt acagtgctta        360
accacattcg aacataccag gcgaaagc                                           388

<210> SEQ ID NO 8
<211> LENGTH: 757
<212> TYPE: DNA
<213> ORGANISM: Artificial Sequence
<220> FEATURE:
<223> OTHER INFORMATION: Synthesized

<400> SEQUENCE: 8
tgaccttcca cgacagatta gtgactgagt acaaggcctc tgtggacatg cctgcgcttg         60
acattaggaa gaagatggaa gaaacggaag tgatgtacaa tgcactttca gagttatcgg        120
tgttaaggga gtctgacaaa tttgatgttg atgtttttc ccagatgtgc aatctttgg         180 aagttgaccc aatgacggca gcgaaggtta tagtcgcggt catgagcaat gagagcggtc        240
tgactctcac ttttgaacga cctactgagg cgaatgttgc gctagcttta caggatcaag        300
agaaggcttc agaaggtgct ttggtagtta cctcaagaga agttgaagaa ccgtccatga        360
agggttcgat ggccagagga gagttacaat tagctggtct tgctggagat catccggagt        420
cgtcctattc taagaacgag gagatagagt ctttagagca gtttcatatg gcaacggcag        480
attcgttaat tcgtaagcag atgagctcga ttgtgtacac gggtccgatt aaagttcagc        540
aaatgaaaaa ctttatcgat agcctggtag catcactatc tgctgcggtg tcgaatctcg        600
tcaagatcct caaagataca gctgctattg accttgaaac ccgtcaaaag tttggagtct        660
tggatgttgc atctaggaag tggttaatca aaccaacggc caagagtcat gcatggggtg        720
ttgttgaaac ccacgcgagg aagtatcatg tggcgct                                 757

<210> SEQ ID NO 9
<211> LENGTH: 57
<212> TYPE: DNA
<213> ORGANISM: Artificial Sequence
<220> FEATURE:
<223> OTHER INFORMATION: Synthesized

<400> SEQUENCE: 9
attctctaga agcttaatac gactcactat agggatgtct tacagtatca ctactcc           57

<210> SEQ ID NO 10
<211> LENGTH: 51
<212> TYPE: DNA
<213> ORGANISM: Artificial Sequence
<220> FEATURE:
<223> OTHER INFORMATION: Synthesized

<400> SEQUENCE: 10
attctctaga agcttaatac gactcactat agggagttgc aggaccagag g                 51

<210> SEQ ID NO 11
<211> LENGTH: 50
<212> TYPE: DNA
<213> ORGANISM: Artificial Sequence
<220> FEATURE:
<223> OTHER INFORMATION: Synthesized

<400> SEQUENCE: 11
```
attctctaga agcttaatac gactcactat aggggggaaag agccgacgag    50

<210> SEQ ID NO 12
<211> LENGTH: 52
<212> TYPE: DNA
<213> ORGANISM: Artificial Sequence
<220> FEATURE:
<223> OTHER INFORMATION: Synthesized

<400> SEQUENCE: 12
attctctaga agcttaatac gactcactat aggggcaagc ctgattgaca ta    52

<210> SEQ ID NO 13
<211> LENGTH: 51
<212> TYPE: DNA
<213> ORGANISM: Artificial Sequence
<220> FEATURE:
<223> OTHER INFORMATION: Synthesized

<400> SEQUENCE: 13
attctctaga agcttaatac gactcactat agggtcttac cgtcgatgtt t    51

<210> SEQ ID NO 14
<211> LENGTH: 50
<212> TYPE: DNA
<213> ORGANISM: Artificial Sequence
<220> FEATURE:
<223> OTHER INFORMATION: Synthesized

<400> SEQUENCE: 14
attctctaga agcttaatac gactcactat aggggttctt gttcggcact    50

<210> SEQ ID NO 15
<211> LENGTH: 52
<212> TYPE: DNA
<213> ORGANISM: Artificial Sequence
<220> FEATURE:
<223> OTHER INFORMATION: Synthesized

<400> SEQUENCE: 15
attctctaga agcttaatac gactcactat agggcttact cccggcctc ta    52

<210> SEQ ID NO 16
<211> LENGTH: 52
<212> TYPE: DNA
<213> ORGANISM: Artificial Sequence
<220> FEATURE:
<223> OTHER INFORMATION: Synthesized

<400> SEQUENCE: 16
attctctaga agcttaatac gactcactat aggggctttc gcctggtatg tt    52

<210> SEQ ID NO 17
<211> LENGTH: 51
<212> TYPE: DNA
<213> ORGANISM: Artificial Sequence
<220> FEATURE:
<223> OTHER INFORMATION: Synthesized

<400> SEQUENCE: 17
attctctaga agcttaatac gactcactat agggtgacct tccacgacag a    51

<210> SEQ ID NO 18
<211> LENGTH: 51
<212> TYPE: DNA

```
<213> ORGANISM: Artificial Sequence
<220> FEATURE:
<223> OTHER INFORMATION: Synthesized

<400> SEQUENCE: 18
attctctaga agcttaatac gactcactat agggagcgcc acatgatact t            51

<210> SEQ ID NO 19
<211> LENGTH: 20
<212> TYPE: DNA
<213> ORGANISM: Artificial Sequence
<220> FEATURE:
<223> OTHER INFORMATION: Synthesized

<400> SEQUENCE: 19
caaggaaatc accgctttgg                                                20

<210> SEQ ID NO 20
<211> LENGTH: 18
<212> TYPE: DNA
<213> ORGANISM: Artificial Sequence
<220> FEATURE:
<223> OTHER INFORMATION: Synthesized

<400> SEQUENCE: 20
aagggatgcg aggatgga                                                  18

<210> SEQ ID NO 21
<211> LENGTH: 20
<212> TYPE: DNA
<213> ORGANISM: Artificial Sequence
<220> FEATURE:
<223> OTHER INFORMATION: Synthesized

<400> SEQUENCE: 21
caaggaaatc accgctttgg                                                20

<210> SEQ ID NO 22
<211> LENGTH: 18
<212> TYPE: DNA
<213> ORGANISM: Artificial Sequence
<220> FEATURE:
<223> OTHER INFORMATION: Synthesized

<400> SEQUENCE: 22
aagggatgcg aggatgga                                                  18
```

The invention claimed is:

1. An RNAi nano-preparation comprising double stranded RNA (dsRNA) of SEQ ID NO: 1 and chitosan, with volume ratio of chitosan to 1 μg/μl dsRNA of 10:1-6.

2. A method of preparing the RNAi nano-preparation of claim 1, comprising dropwise adding dsRNA solution into chitosan non material solution in proportion, uniformly mixing, slowly adding the dsRNA-containing chitosan solution into a 1% SDS solution at a ratio of 2:1, shaking for 10 minutes and wrapping the dsRNA inside the chitosan to form spheroids with a diameter of 100-200 nm; wherein the concentration of the dsRNA solution is 1 μg/μl; chitosan nano material solution is prepared by dissolving chitosan in glacial acetic acid and the final concentration of the chitosan nano material solution is 2 μg/μl.

3. A method of tobacco mosaic virus prevention comprising uniformly spreading or spraying a solution of claim 1 on plant leaves.

* *